(12) United States Patent
Knoll

(10) Patent No.: US 8,201,473 B2
(45) Date of Patent: Jun. 19, 2012

(54) WORM-LIKE MECHANISM

(75) Inventor: Alois Knoll, Melle (DE)

(73) Assignee: Robotics Technology Leaders GmbH, Munich (DE)

( * ) Notice: Subject to any disclaimer, the term of this patent is extended or adjusted under 35 U.S.C. 154(b) by 402 days.

(21) Appl. No.: 12/445,426

(22) PCT Filed: Oct. 12, 2007

(86) PCT No.: PCT/EP2007/008897
§ 371 (c)(1),
(2), (4) Date: Jun. 1, 2009

(87) PCT Pub. No.: WO2008/046566
PCT Pub. Date: Apr. 24, 2008

(65) Prior Publication Data
US 2009/0314119 A1    Dec. 24, 2009

(30) Foreign Application Priority Data

Oct. 13, 2006  (DE) .......................... 10 2006 048 531

(51) Int. Cl.
*B25J 17/00*    (2006.01)

(52) U.S. Cl. .................................. 74/490.05

(58) Field of Classification Search ............... 74/490.04, 74/490.05, 110; 92/90–92, 64, 42, 47; 600/116, 600/141; 604/97.03, 100.03, 121, 920; 606/166, 606/192

See application file for complete search history.

(56) References Cited

U.S. PATENT DOCUMENTS

| 3,284,964 | A |   | 11/1966 | Saito |
|---|---|---|---|---|
| 4,784,042 | A | * | 11/1988 | Paynter ........................... 91/534 |
| 5,251,538 | A | * | 10/1993 | Smith ............................... 92/34 |
| 5,337,732 | A |   | 8/1994 | Grundfest et al. |
| 5,386,741 | A |   | 2/1995 | Rennex |
| 5,469,756 | A | * | 11/1995 | Feiten ....................... 74/490.05 |
| 5,897,488 | A |   | 4/1999 | Ueda |
| 6,772,673 | B2 | * | 8/2004 | Seto et al. ......................... 92/92 |

FOREIGN PATENT DOCUMENTS

| DE |     4240435 | A1 | 5/1994 |
|---|---|---|---|
| DE |     4408730 | A1 | 9/1995 |
| DE |    19833340 | A1 | 2/2000 |
| EP |     0017016 | A  | 10/1980 |
| EP |     0249318 | A  | 12/1987 |
| JP |    05293787 | A  | 11/1993 |

* cited by examiner

*Primary Examiner* — Robert Pezzuto
(74) *Attorney, Agent, or Firm* — Muncy, Geissler, Olds & Lowe, PLLC

(57) ABSTRACT

The invention relates to a worm-like mechanism comprising a support structure, which extends in the longitudinal direction of the mechanism, and at least two actuating units, which are arranged one behind the other in the longitudinal direction of the support structure and each of which has two supporting elements, which while extending transversely in relation to the longitudinal direction of the support structure are attached to the latter at a distance from one another in the longitudinal direction, and at least one actuating element, which is arranged between the supporting elements and by which the supporting elements can be moved in relation to one another. In order to provide a further worm-like mechanism, which provides precise open-loop or closed-loop control of its movements while in particular being of a simplified, slender construction, it is provided that the actuating elements can be activated individually or in group by way of a central line.

27 Claims, 8 Drawing Sheets

WORM-LIKE MECHANISM

BACKGROUND OF THE INVENTION

The invention relates to a worm-like mechanism, in particular a worm-type or serpentine deformable handling mechanism.

Worm-like or serpentine mechanisms, for example for endoscopy, that consist of a continuously deformable carrier, are known. Provided perpendicularly at specific spacings on this carrier are disks with fastening points that are connected to the ends of wire ropes that are carried along on the carrier. If one or more of these wire ropes is tensioned, this leads to a curvature of the mechanism.

DE 198 33 340 A1 further discloses a worm-like working mechanism that has as central supporting element a stretch-elastic restoring device on which disk-shaped supporting elements are fitted perpendicularly at specific spacings. Provided around the central stretch-elastic restoring device are three actuators that respectively consist of a row of pockets or pads lying one against another. The individual pockets or pads respectively lie in this case between two supporting elements. A liquid or gaseous pressure medium can be fed to each of these actuators via a dedicated access channel such that the pads of the actuators occupy different volumes depending on the filling state. The pads press one another apart. If pressure medium is applied uniformly to the three actuators, the result is a change in the length of the working mechanism. If pressure medium is applied differentially to the three actuators, this produces a corresponding curvature of the working mechanism. Individually or in groups, the pads are hereby respectively equipped with a dedicated feed for the pressure medium.

U.S. Pat. No. 3,284,964 discloses a serpentine, flexible gripper arm structure that has three sections each having a multiplicity of actuating units. The feeding of a working medium to an actuating unit or group of actuating units that respectively consist of pads or bellows arranged between supporting elements is performed starting from a central unit at which the control of the working pressure is undertaken for each actuating unit or group of actuating units. This central unit is located outside the flexible gripper arm structure and is normally large and heavy. Above all, however, this design results in large line lengths, the consequence of the dead times resulting therefrom being a poor capability for open-looped or closed-loop control of the mechanism. Moreover, the base of the gripper arm, through which all the lines are guided, has a large circumference that grows with the length of the gripper arm and/or the number of segments. The result of this is that such mechanisms normally become very thick in relation to their length, and so their mobility is substantially restricted.

Instead of using pressure pads or bellows that expand upon pressure application and effect a lengthening, it is also possible to use so-called artificial muscles such as are available from Festo AG & Co. KG, Esslingen, Germany.

It is the object of the invention to provide a further worm-like mechanism whose movements can be subjected to precise open-loop or closed-loop control in conjunction, in particular, with a simplified, slim design.

This object is achieved by the worm-like mechanism as claimed in claim 1. Advantageous refinements and developments of the invention are described in the subclaims.

BRIEF SUMMARY OF THE INVENTION

Thus, according to the invention, in the case of a worm-like mechanism having a support structure extending in the longitudinal direction of the mechanism, and at least two actuating units arranged one behind another in the longitudinal direction of the support structure, of which each has two supporting elements and at least one actuating element that is arranged between the supporting elements and by means of which the supporting elements can be moved relative to one another, it is provided that the actuating elements can be activated individually or in groups via a central line.

The central activation of the actuating elements in the actuating units for the purpose of deforming the mechanism via a central line that extends along the worm-like mechanism enables short switching times that is also suitable for individual correction of the movements or deformations attained by the individual actuating units.

Conventional electric or magnetic actuators can also be used in principle as actuating elements. In a preferred design of the invention, however, it is provided that the actuating elements are hydraulic or pneumatic actuating elements, that the central line is a feed line for feeding a hydraulic or pneumatic working medium to the actuating elements, and that each of the actuating elements is connected individually or in groups to the feed line via a valve.

When use is made of hydraulic or pneumatic actuating elements, the working medium is therefore fed to the individual actuating elements by a central line that can be designed as a tube or hose which is pressurized such that the working medium or pressure medium can quickly be fed without substantial dead times to the individual actuating elements via the valves connected to the central feed line. Since the valves are arranged near the actuating elements, extremely short feed paths to the actuating elements result, and so it is possible for the effective switching times to be drastically shortened.

It is expediently provided in this case that the valves in each case have a first open position for connecting the actuating element(s) to the feed line, a closed position and a second open position for letting the working medium out of the actuating element(s).

It is also conceivable in principle that, in order to relieve the pneumatic or hydraulic actuating elements, in their second open position the valves connect the actuating elements to the surroundings if use is made as working medium of a gas or a liquid that can be vented or drained into the surroundings without endangering the environment or the work environment in which the mechanism is used. However, it is expediently provided that in the second open position the valves connect the actuating elements to a return line or to an outlet line. It is thereby possible to obtain either a recovery of the working medium or a discharge of the working medium into a region where the work environment of the mechanism is not impaired, and this is necessary for a multiplicity of applications such as, for example, in endoscopy, and expedient in virtually all applications, since the field in which the worm-like mechanism can work or be used is not impaired.

The return line can also be designed as a suction or reduced pressure line, and be connected to an appropriate vacuum source in order to accelerate the pressure reduction in the actuating elements.

In an advantageous development of the invention, it is provided that the valves can be switched by means of a structure of stacked piezoelements. The result of this is that the valves can be switched quickly and reliably.

The use of such very quickly controllable valves, and the short or even absent lines between valve outlet and actuating element enable extremely high frequencies in controlling the valves, with the result that it is possible, for example, to set compliances of the actuating elements when venting pressure, and thus that the pressure of the actuating elements is slowly reduced in a defined fashion for the purpose of passively changing length such that it is possible for opposing torques of the mechanism to be finely set and regulated.

In accordance with an expedient development of the invention, it is provided that each actuating unit has a driver circuit that is connected to a central control circuit and that supplies switching signals for the valves of the actuating unit as a function of control information received from the central control circuit, the driver circuit comprising an open-loop information processing circuit that generates control signals for the valve driver circuits switching the valves as a function of the received open-loop control information.

In order, for the purpose of closed-loop control, to detect the movements and/or deformations respectively achieved, it is provided in accordance with the invention that each actuating unit has one or more movement sensors whose output signals are detected by the driver circuit.

If, in this case, the actuating information is determined centrally for each actuating element, it is expedient when the driver circuit has a transmission circuit for transmitting the output signals from the movement sensor(s) to the central control circuit.

However, it is also possible for the driver circuit to have a closed-loop controller circuit, to which as closed-loop control information, the open-loop control information received from the central control circuit and the output signals from the movement sensor(s) are fed, and that supplies open-loop control signals for the valve driver circuits switching the valves as a function of the closed-loop control information.

Provided expediently as movement sensors for buckling, longitudinal or rotary movements can be one or more strain gauges that are fitted on the support structure. In addition, it is possible for one or more plunger coils to be arranged between the supporting elements of the actuating unit such that they detect the relative movement of the supporting elements. In another refinement of the invention, it is provided that provided as movement sensor is an optical position detector with a light source and a position-sensitive photoreceiver that are respectively arranged on elements of the actuating unit that can be moved toward one another, the position detector supplying an output signal corresponding to the relative movement between these elements.

It is possible to provide as actuating elements pressure cylinders, pneumatic or hydraulic working pads expanding under pressure or else pneumatic or hydraulic working elements contracting under pressure, in particular so-called artificial muscles. It is also possible in this case to combine the different length-varying actuating elements with one another depending on the desired movement sequences and the capability for open-loop or closed-loop control.

It is also possible in this case for the actuating elements to supply a restoring effect upon pressure relief. Furthermore, it is expedient in various applications for one or more restoring elements to be assigned to the actuating elements.

If one or more oppositely acting actuating elements are assigned to each actuating element of an actuating unit, it is then possible for the actuating elements to adopt the role of muscles that cooperate as protagonist and antagonist in order to be able to execute a defined movement very precisely.

In an expedient development of the invention, it is provided that the actuating element(s) is/are arranged in the actuating unit such that upon activation they effect a change in length.

It is expedient for most applications that two, three or more actuating elements are arranged in an actuating unit such that upon appropriate activation they effect a defined tilting of the two supporting elements toward one another in a defined radial direction.

In accordance with another refinement of the invention, it is provided that the actuating elements are arranged in an actuating unit such that upon activation they effect a rotation of the two supporting elements about the longitudinal direction of the support structure.

Depending on the application, it is possible in a worm-like mechanism in accordance with the present invention to combine with one another various actuating units that respectively effect only a change in length or a bending or tilting or a rotation about the axis of the worm-like mechanism. However, it is also possible to combine the various movements in one actuating unit, the central carrier and/or the bearing of the supporting elements being required to be designed such that the supporting elements of the actuating unit can follow the desired movements and deformations.

The supporting elements are expediently designed as supporting disks that have a passage for the central line. In this case, the passage for the central line need not lie in the region of the central axis of the mechanism, but can also be laterally offset therefrom. The central line is respectively to be designed in this case such that it can directly follow the movements of the individual actuating units without disturbing the latter.

It is provided in another advantageous refinement of the invention that the support structure has a continuously deformable tubular or hose-like carrier on which the supporting element are fastened at defined axial spacings. The use of a tubular or hose-like carrier as support structure of the mechanism enables the respective feed and discharge lines and the electrical open-loop control lines to be guided with additional protection through the worm-like mechanism. However, it is also conceivable to use the tubular or hose-like carrier itself as feed line for the working medium, the result being further simplification of the design.

In another refinement of the invention, it is provided that the support structure consists of a plurality of similar support segments that are modularly interconnected.

The use of a support structure similar to the spinal column and consisting of support segments of the same type allows a substantial rationalization of the production of worm-like mechanisms of various types, in particular of different lengths, it thereby being possible to reduce production costs. The modular support segments can in this case also consist of tubular or hose-like carriers having supporting elements arranged thereon, the tubular or hose-like support sections requiring to be equipped at their ends with appropriate coupling members such that the finished, worm-type mechanism constructed therefrom has as support structure a continuous, deformable carrier that is assembled from individual sections.

In another refinement of the invention, it is provided that each of the actuating units has a support segment that comprises a first supporting disk that is permanently connected to one end of a longitudinal carrier, and a second supporting disk that is held pivotably and/or rotatably on the other end of the longitudinal carrier via an articulated connection, the first supporting disk having, on its side averted from the longitudinal carrier, fastening means for fastening a second supporting disk of an adjacent support segment.

In accordance with another embodiment of the invention, it is expedient when each of the actuating units comprises a support segment that has a supporting disk that is permanently connected to one end of a longitudinal carrier and that carries an articulated bearing on its side averted from the longitudinal carrier, the longitudinal carrier carrying on its other end an articulated member corresponding to the articulated bearing such that the longitudinal carrier of an actuating unit can be pivotably and/or rotatably supported in the articulated bearing on the supporting disk of the next actuating unit.

In order, in the case of a known position of use for the worm-like mechanism, to attain pretensioning in a preferred direction or relief from statically bearing forces, such as gravity, for example, it is expedient when provided in one or more of the actuating units are tension and/or compression spring elements that support the mechanism internally in order to balance static forces which are to be expected in a planned position of use of said mechanism. It is thereby possible for the individual actuating elements really to have to apply no more than the differential force for the desired movement or adjustment.

In order to provide particularly slim, worm-like mechanisms that can be used, for example, in endoscopy in order to examine the human or animal body, it is advantageous when provided as actuating elements are piezoelectric actuators that can be subjected to open-loop or closed-loop control by the driver circuit. Precisely in the case of endoscopic examination of the human body, it is advantageous to work with worm-like mechanisms that are as slim as possible in order to damage the body and load the patient as little as possible.

BRIEF DESCRIPTION OF THE DRAWINGS

The invention is explained in more detail below by way of example with the aid of exemplary embodiments illustrated in the drawing, in which.

DETAILED DESCRIPTION

Figure 1:
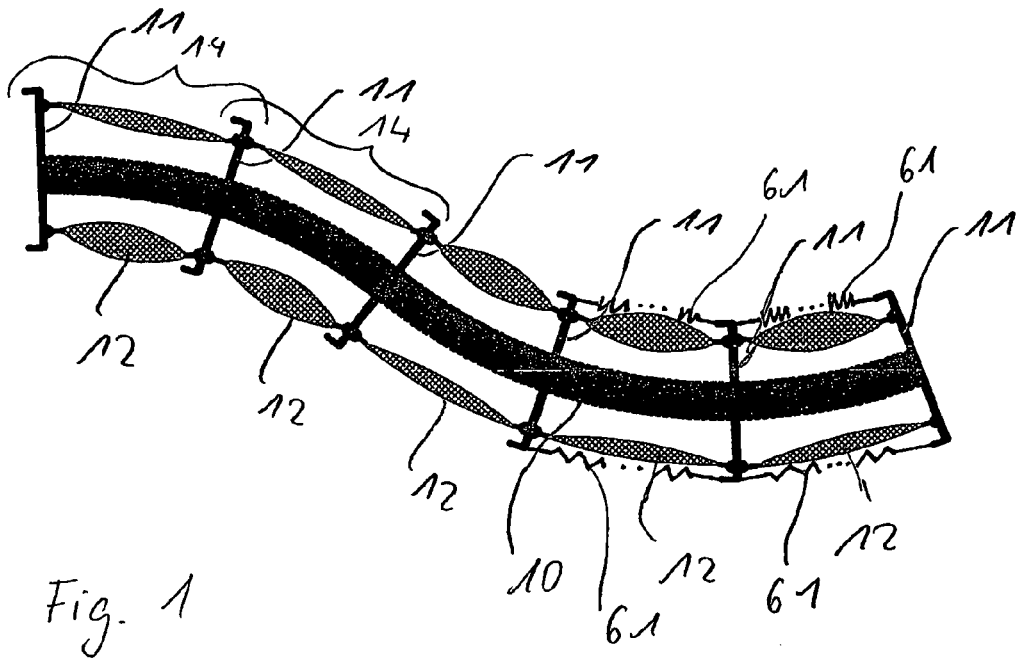
FIG. 1 shows a greatly simplified schematic of a worm-like mechanism in accordance with the invention having a continuously deformable support structure.

Mutually corresponding components and circuit elements are provided throughout with the same reference symbols in the various figures of the drawing.

FIG. 1 shows a first embodiment of an inventive worm-like mechanism having a support structure 10 that is designed as a continuously deformable carrier, as is explained in more detail below. Arranged on the support structure 10 are supporting elements 11 that can, for example, be designed as plates or disks, but also as supporting struts arranged in the manner of stars or crosses.

Arranged between two supporting elements 11 adjacent in the longitudinal direction of the support structure are actuating elements 12 that are indicated in FIG. 1 as artificial muscles that shorten upon pressure application.

The supporting elements 11, which extend transverse to the longitudinal direction of the support structure 10 are fitted on the latter in a fashion spaced apart from one another in the longitudinal direction of the support structure 10. In this case, two adjacent supporting elements 11 respectively form an actuating unit 14 together with the actuating elements 12 lying therebetween and the section of the support structure 10 between the actuating elements 12, the supporting elements 11 respectively belonging to two adjacent actuating units 14 in the case of the embodiment of the invention illustrated in FIG. 1.

Figure 2:
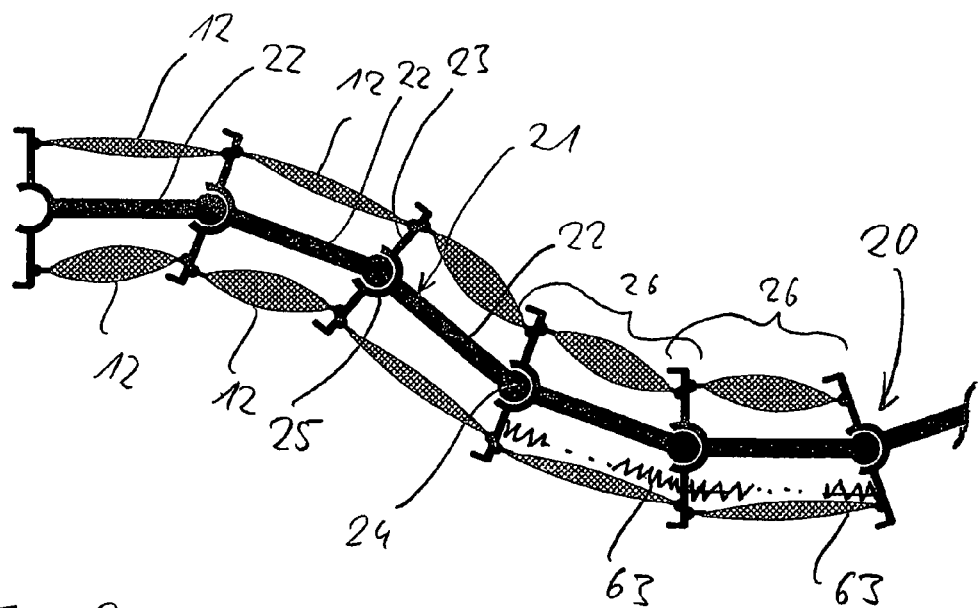
FIG. 2 shows a greatly simplified schematic of a worm-like mechanism in accordance with the invention of a deformable support structure with an arrangement of the support segments that resembles a spinal column.

FIG. 2 shows another deformable, worm-like mechanism in accordance with the present invention, in the case of which the support structure 20 is designed like a spinal column and has support segments 21 of which each has a longitudinal carrier 22 and a supporting disk 23. The longitudinal carrier 22 is designed at its end averted from the supporting disk 23 as an articulated member 24 that is accommodated in an articulated bearing 25 formed on the supporting disk 23 and/or the longitudinal carrier 22 of the adjacent actuating unit 26.

The articulated member 24 and the articulated bearing 25 are illustrated in FIG. 2 as elements of a ball joint that enables both pivoting and rotary movements. However, it is also conceivable that the articulated connection between two actuating units 26 of the mechanism are designed such that it permits either only a rotary movement about the longitudinal axis of the mechanism, or a pivoting or tilting movement relative to the longitudinal axis of the mechanism with one or two degrees of freedom. The design of articulated member and articulated bearing is in this case to be designed in dependence on the requirements of the application and the forces to be transmitted.

Figure 3:
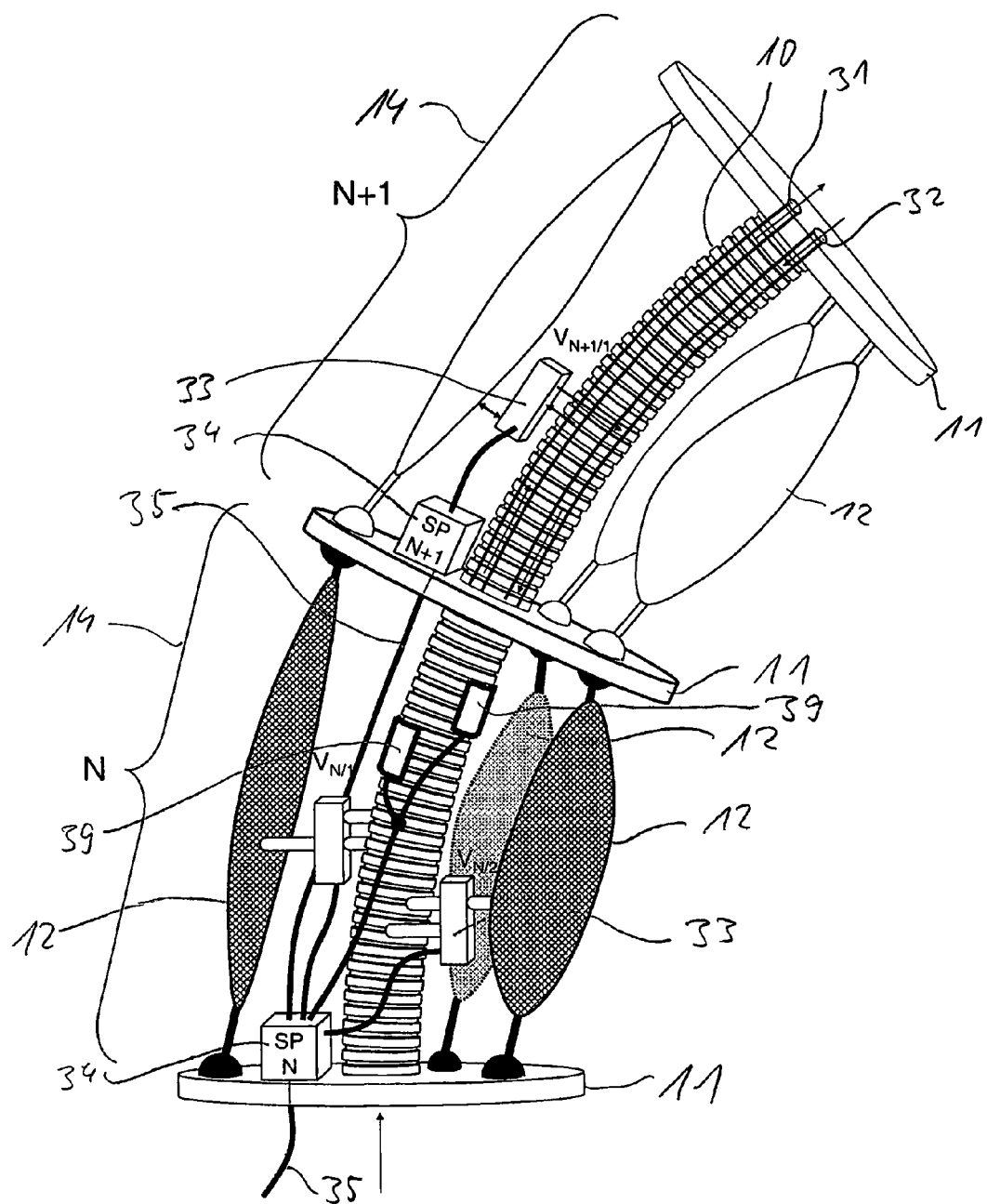
FIG. 3 shows a simplified, perspective schematic of two actuating units, adjoining one another, of the worm-like mechanism in accordance with a first exemplary embodiment of the invention.

FIG. 3 shows the Nth and (N+1)th actuating unit 14 of a worm-like mechanism that has a continuously deformable support structure 10 as indicated in FIG. 1. In accordance with FIG. 3, the continuous support structure 10 is formed, for example, from a supporting hose that consists of annular, interlocking and mutually displaceable supporting rings. Instead of providing such a supporting hose through which it is possible to guide directly not only one or more central lines 31, 32 and if appropriate, also data lines, but also, in accordance with another refinement, a working medium for the individual actuating elements 12, it is also possible to provide a corrugated hose or a flexible, lattice-like hose or tube structure. In this case, the support structure 10 has a certain stiffness, which is to be adapted in dependence on the application of the mechanism.

The support structure 10 can also be constructed from supporting hose sections that are coupled to one another in a suitable way at the transitions between the actuating units 14 in order to obtain a modular structure.

Circular supporting disks 11 are arranged as supporting elements on the support structure 10, there being arranged between the two supporting disks 11 of an actuating unit 14 in the illustrated exemplary embodiment three actuating elements 12 that are indicated as artificial muscles and are positioned in a distributed fashion around the support structure 10 in a circumferential direction. Depending on the field of use, the circumferential distribution of the actuating elements 12 can be uniform or non-uniform. The latter is the case, in particular, whenever the radial force effect is also non-uniform in the state of rest as, for example, in the case of a horizontal application as a result of gravity.

Figure 6:
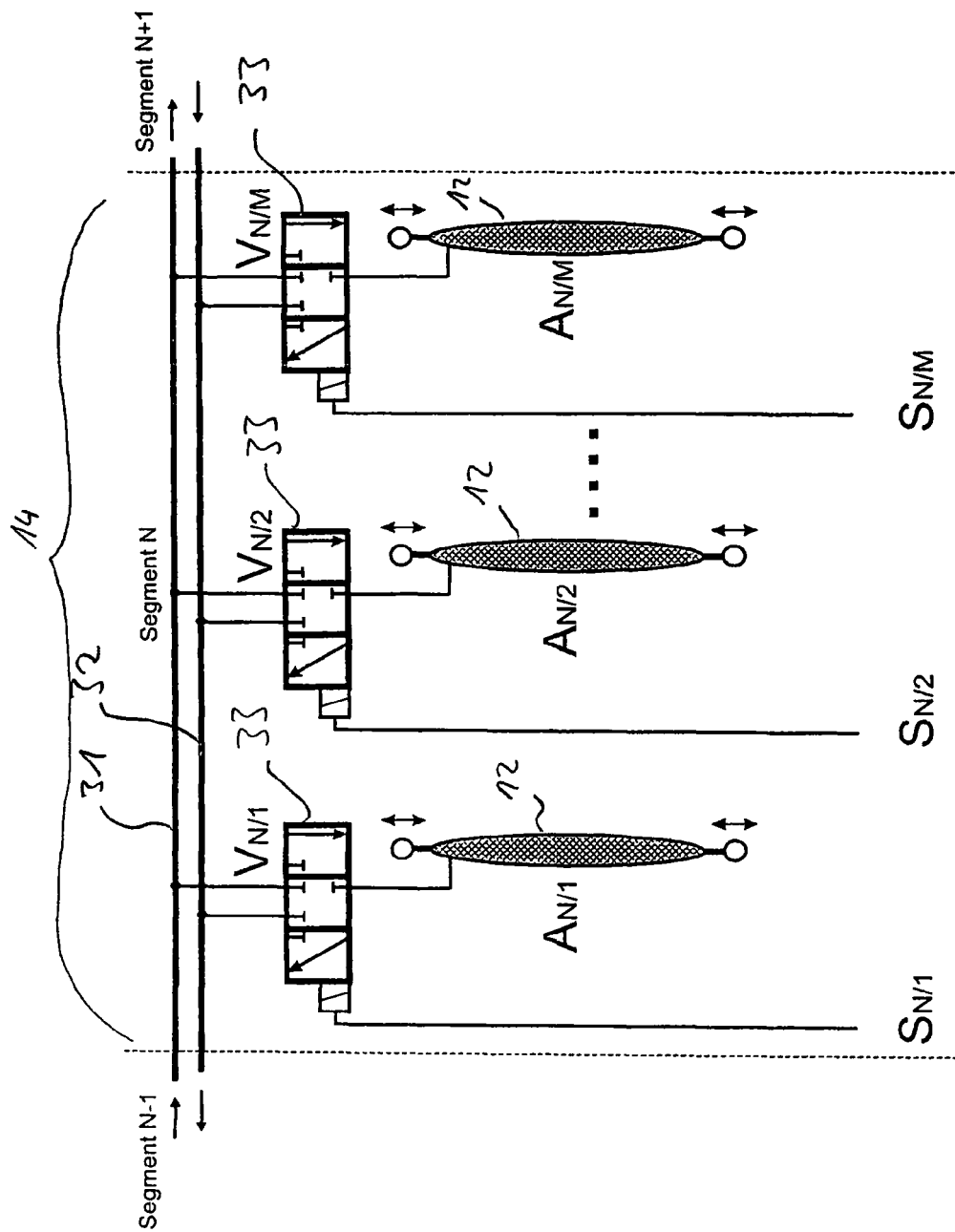
FIG. 6 shows a simplified schematic hydraulic/pneumatic circuit diagram in order to illustrate the application of pressure to artificial muscles used as actuating elements.

As is illustrated in FIGS. 3 and 6, three actuating elements 12 can be connected via assigned valves 33 to the feed line 31 for feeding a hydraulic or pneumatic working medium, and to an outlet line or return line 32 for the working medium.

As is shown in FIG. 6, the valves 33 are designed as 3/3-way valves that have a central closed position and a first open position, in which the actuating elements 12 are connected to the feed line 31, and a second open position, in which the actuating elements 12 are connected to the return line or outlet line 32.

Instead of the connection of the actuating elements 12 to the return line or outlet line 32 for letting out working medium, the valves 33 can also be designed such that they connect the actuating elements 12 directly to the environment if, for example, use is made as working medium of air that, in many applications, can be readily vented to the outside without damaging the environment. Correspondingly, if the mechanism is used underwater it is conceivable for water as working medium also simply to be let out into the surroundings. In the case of other applications, for example in medicine, it is, however, necessary for the working medium to be guided out of the worm-like mechanism and either to be led back into a sump for recovery, or to be discharged into the environment at a point where this is harmless for the handling of the worm-like mechanism.

The valves 33 can be designed as solenoid valves that can be switched quickly and reliably. If the pressure in the actuating elements 12 needs to be controlled not only in an open-loop fashion, but also in a closed-loop fashion, and if the open-loop control valves 33 are required for this purpose to be capable of switching with a high frequency and very quickly and reliably, a structure composed of stacked piezoelements is suitable for the purpose. Beside such valves and classic solenoid valves, it is also possible to use valves that are actuated by piezomotors.

Figure 8:
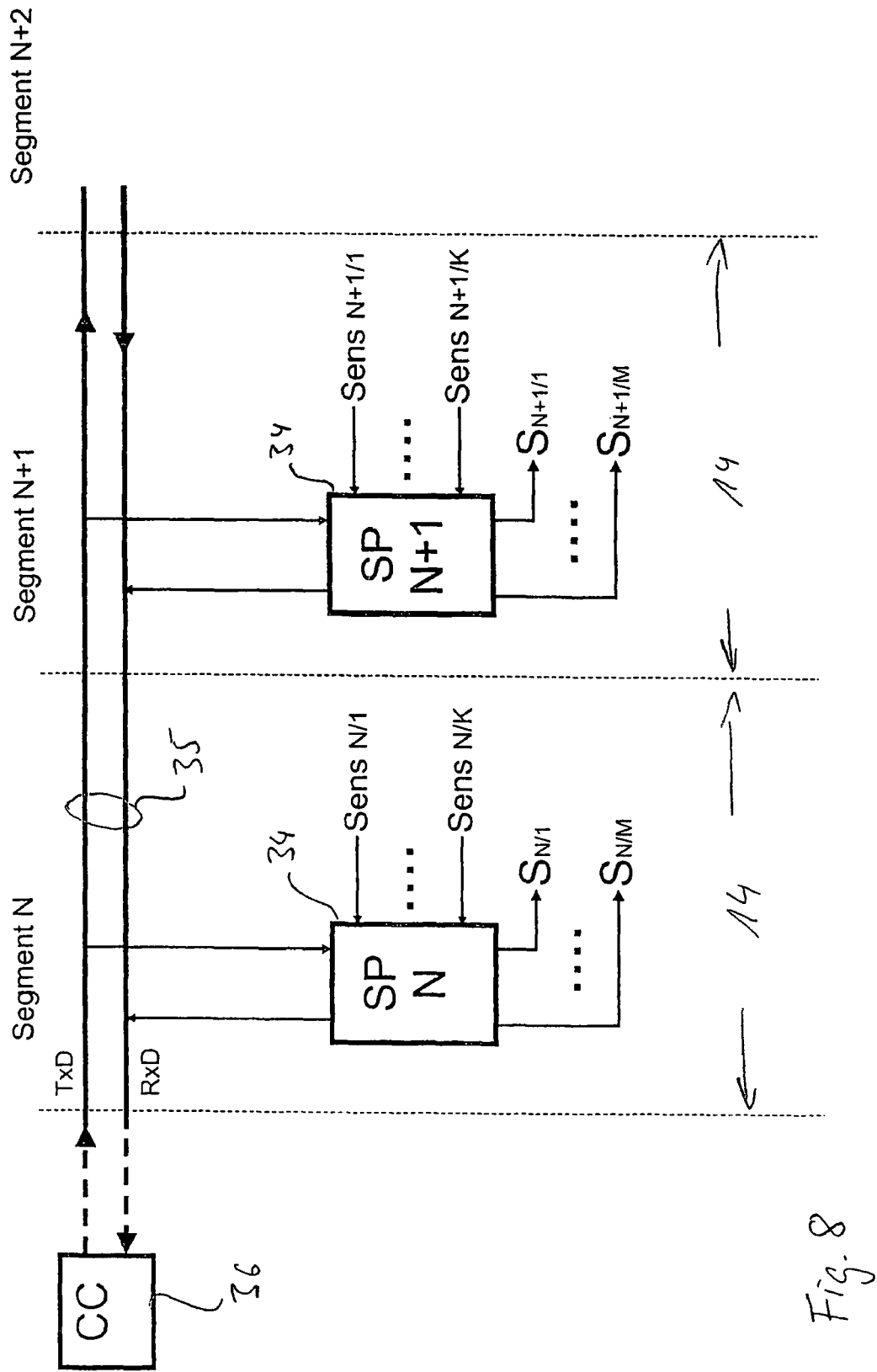
FIG. 8 shows a simplified schematic circuit diagram for the purpose of illustrating the electrical activation of the individual actuating units.
Figure 9:
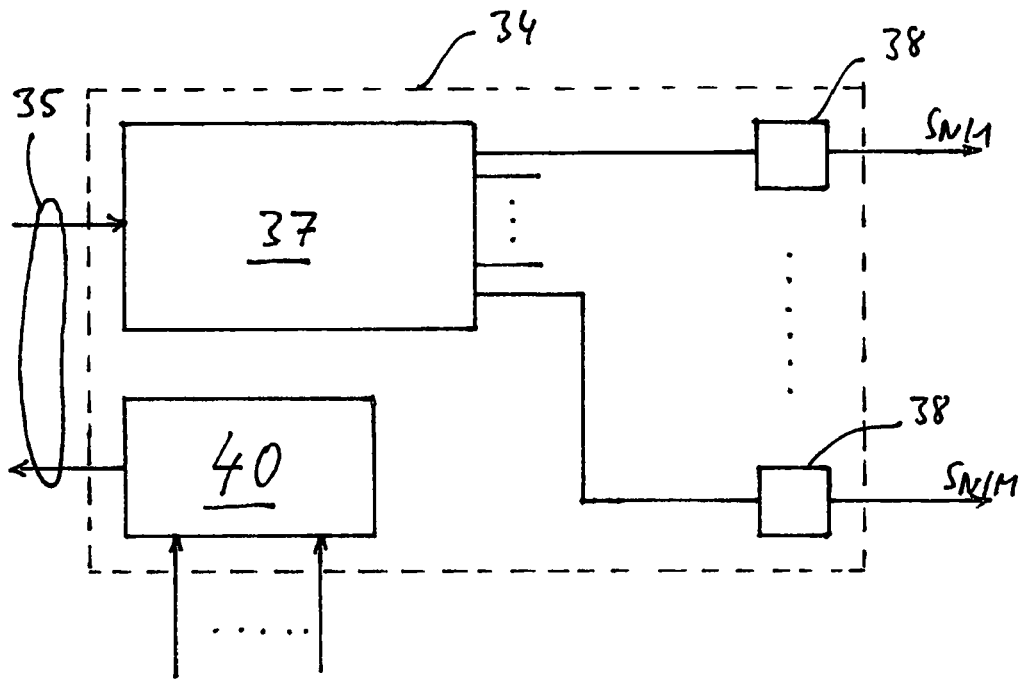
FIG. 9 shows a simplified schematic block diagram of a driver circuit in the actuating units.
Figure 10:
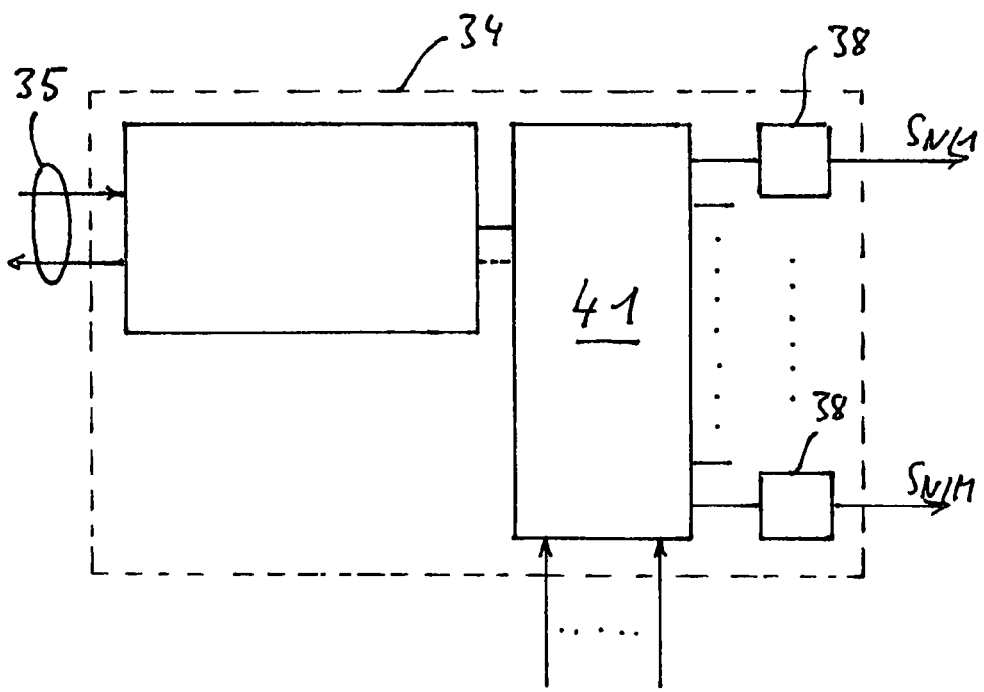
FIG. 10 shows a simplified schematic block diagram of another driver circuit of the actuating units.

As is illustrated in FIGS. 3 and 8, each actuating unit 14 has a driver circuit 34 that is connected via a bus 35 to a central control circuit 36. The driver circuit 34, which supplies switching or open-loop control signals $S_{N/1}, \ldots, S_{N/M}$ for the valves 33 of the actuating unit 14 as a function of the central control circuit 36, can comprise an open-loop control information processing circuit 37 (see FIG. 9), that is informed by the central control circuit 36 of the control data for the corresponding valves 33 for the purpose of setting the working pressure required in each of the actuating elements 12.

However, it is also conceivable for the central control circuit 36 to supply the open-loop control information processing circuits 37 of the driver circuits 34 of the individual actuating units 14 only with information or data relating to the movement to be executed by the mechanism, or to the shape to be assumed, whereas the open-loop control information processing circuit 37 in each of the actuating units 14 itself locally determines the corresponding desired values to be set for the individual actuating elements 12 from the received data, and thus applies appropriate working medium to the actuating elements 12 via the valves 33. In order to switch the valves 33, the driver circuit 34 preferably has for each valve 33 a corresponding driver circuit 38 that converts the logical control signals into actuating signals.

In order not only to obtain open-loop control of the relative movement of the two supporting disks 11 of an actuating unit 14 in relation to one another, but also to be able to carry out closed-loop control of the set positions, each actuating unit 14 is advantageously provided with one or more movement sensors 39 whose output signals are supplied to the driver circuit 34.

In the case when the central open-loop control circuit 36 transmits the control data required for the respective actuating elements 12 to the driver circuit 34, that is to say when these data are calculated centrally from the movement to be executed or position to be assumed, the output signals of the movement sensors 39 of the driver circuit 34 can be transmitted back via a transmission circuit 40 and the bus 35 to the central open-loop control circuit 36 that then recalculates the control data for the individual actuating elements 12 for closed-loop control.

If, in accordance with another refinement of the invention, work is performed with the aid of a distributed intelligence or computing capability, and if only information or data relating to the movement to be executed or position to be adopted is supplied to the individual driver circuits 34 of the actuating units 14, and if the open-loop control information processing circuits 37 themselves determine there locally the corresponding control data for the individual actuating elements 14, which are converted by the valve drivers 38 into corresponding control signals $S_{N/1} \ldots S_{N/M}$, it is expedient to provide in each driver circuit 34 a closed-loop controller circuit 41 that determines a changed manipulated value for the recalculation from the desired values of the manipulated values and the actual values, detected via the movement sensors 39, of the deformation achieved.

As movement sensors for detecting the relative movement of the supporting disks 11 of an actuating unit 14 toward one another and the curvature of the support structure 10 in the individual actuating units 14, it is possible to provide sensors, for example strain gauges, on the support structure as movement sensors. However, instead of providing strain gauges it is also possible to provide angle encoders, suitably arranged plunger coils or optical position detectors (see FIG. 4). A plunger coil 62 is indicated for example in FIG. 5(*a*). Such sensors can therefore be used to attain very accurate closed-loop control of the worm-like mechanism, it being advantageous that, particularly when use is made of stacked piezoelements, the valves 33 can be switched very quickly as valve drive such that the quantity of working medium let through for a movement step that is to be attained can be very small, and this results in a corresponding small control step, and thus supplies a high setting accuracy.

In the case of the worm-like mechanism illustrated in FIGS. 1 and 3, the working medium is supplied through the continuously deformable support structure 10. In the case of worm-like working mechanisms that work with a working medium that can readily be released into the corresponding surroundings, it is also possible to provide in this case that the support structure 10 itself serves not only as a supporting or corrugated hose, but also as a pressure hose for feeding the working medium to the individual valves 33.

In addition to the central line 31, 32, guided through the support structure 10, for the working medium, the central line 31, 32 can also be guided outside the support structure 10. This is shown in FIG. 4 in the case of an actuating element 14 of a worm-like mechanism with a support structure 21 resembling a spinal column and which is of modular construction.

Figure 4:
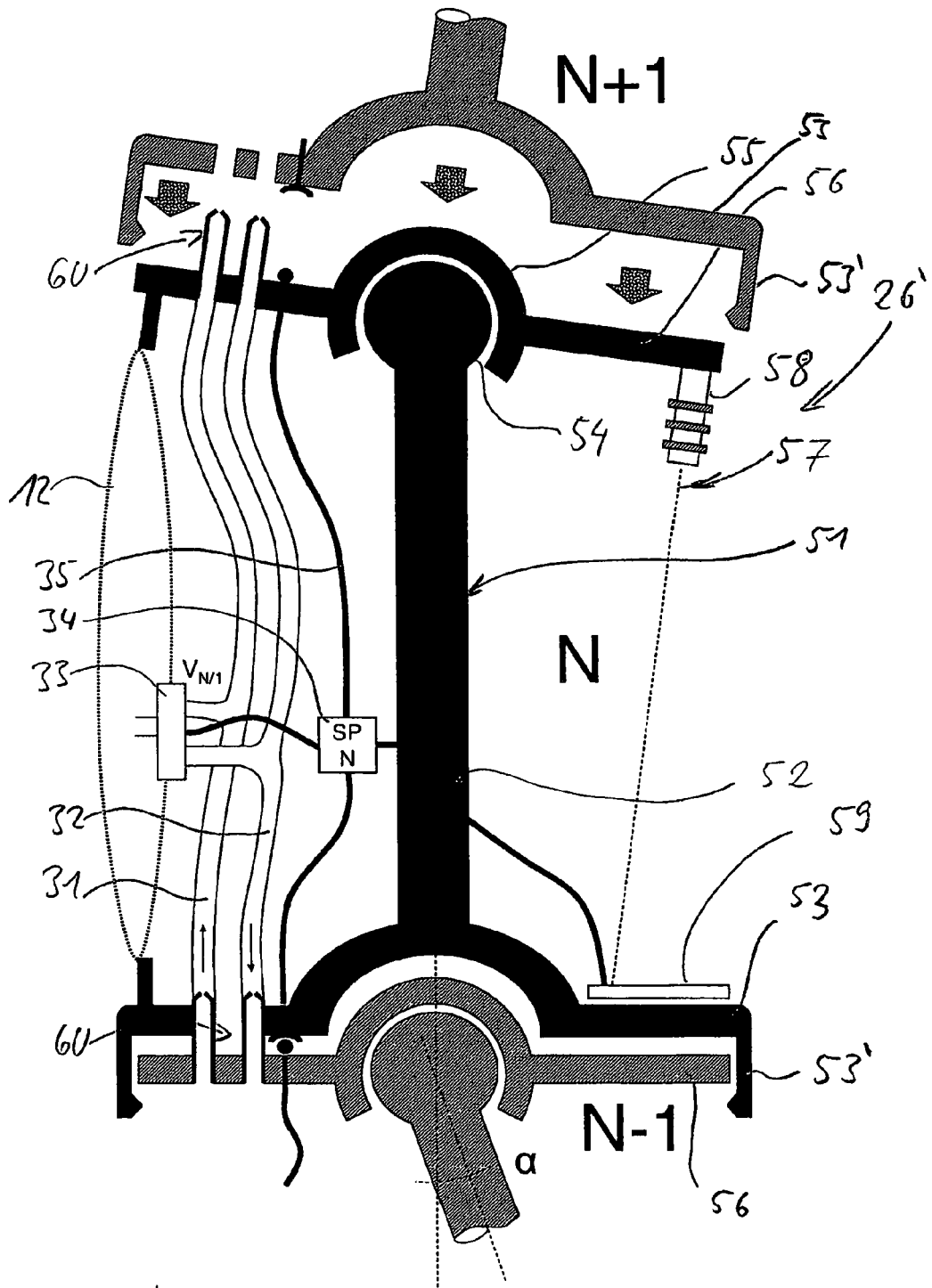
FIG. 4 shows a simplified sectional schematic of an actuating unit of a worm-like mechanism in accordance with another exemplary embodiment of the invention.
Figure 5:
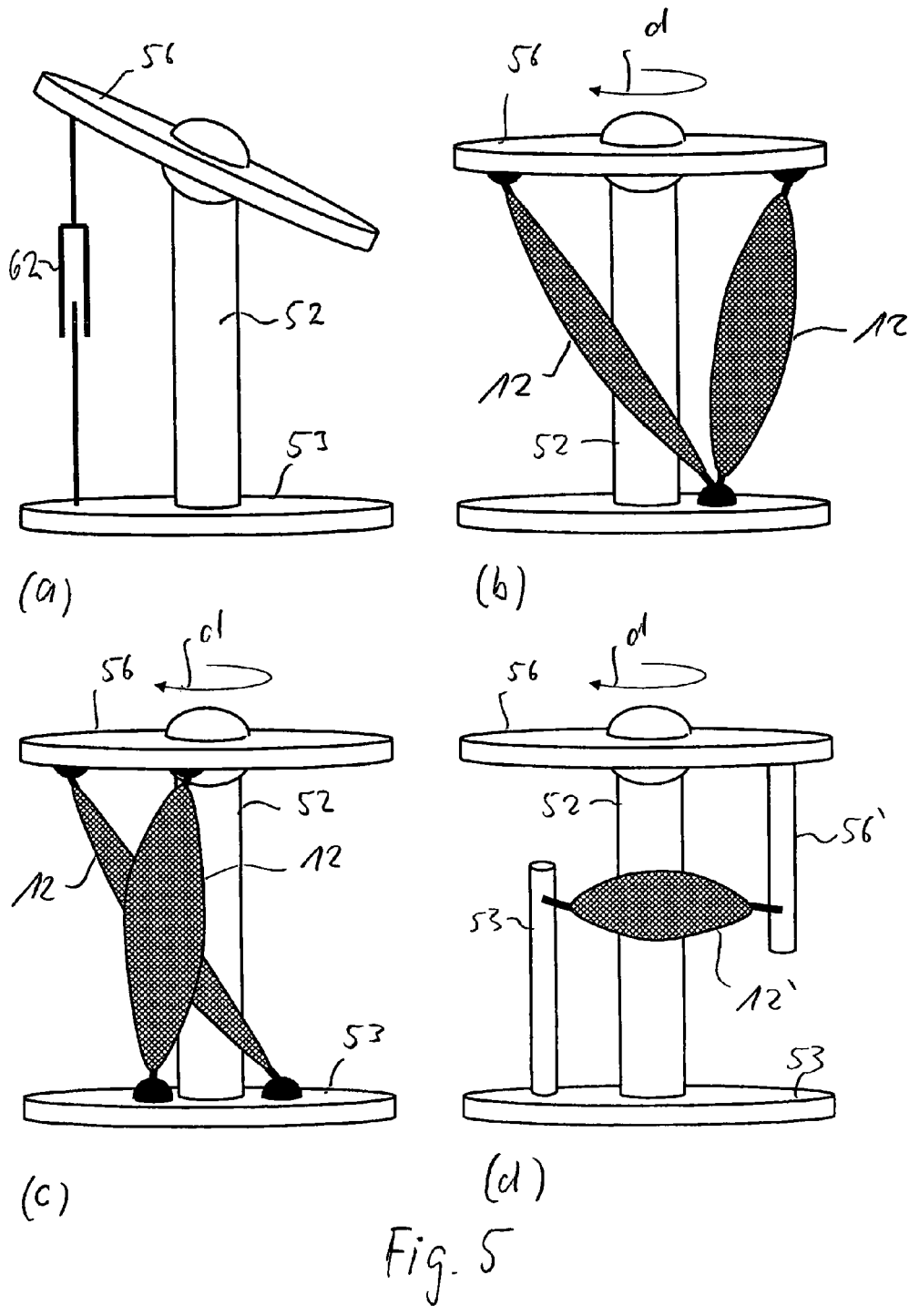
FIGS. 5(a) to (d) show greatly simplified schematic views of an actuating unit of an inventive mechanism for the purpose of demonstrating various possibilities of arranging actuating elements.

In a way similar to that illustrated in FIG. 2, the support structure of the actuating unit 26' in FIG. 4 has a support segment 51 with a longitudinal carrier 52 and a supporting disk 53 arranged thereon. The longitudinal carrier 52 has on its end averted from the supporting disk 53 an articulated member 54 on which there is mounted an articulated bearing 55 that carries a second supporting disk 56. Depending on the desired degrees of freedom of movement, the joint formed by the articulated member 54 and the articulated bearing 55 can enable a rotary movement about the longitudinal axis of the longitudinal carrier 52 and/or a swiveling or tilting movement relative thereto in one or two degrees of freedom.

The first supporting disk 53 has on its side averted from the longitudinal carrier 52 fastening means, indicated as axial flange 53', for holding a second supporting disk 56 of a subsequent or preceding actuating unit 26'.

First and second connecting means 60 indicated as plugs or couplings are provided in the first and second supporting disks in order to interconnect the individual sections of the bus 35, the working medium feed line 31 and the return line or vent line 32 such that the bus 35 and the lines 31, 32 extend continuously through the modularly structured, worm-like mechanism. In the case of a support structure in the form of a spinal column as shown in FIG. 2, the lines 31, 32 and, if appropriate, also the bus 35, can be guided continuously through the mechanism as in the embodiment according to FIG. 3.

Illustrated as movement sensor in FIG. 4 is an optical detector 57 that comprises a light source, preferably a laser 58, in particular a laser diode, and a position-sensitive photo detector 59. Laser 58 and position-sensitive detector 59 are arranged in this case on opposite sides of the first and second supporting disks 53, 56.

Although FIG. 4 illustrates only one actuating element 12 that can be connected via a valve 33 to the feed line 31 and the return line or vent line 32, two, three or more actuating elements 12 can be provided depending on requirements.

Instead of bending the support structure 10 or tilting the two supporting elements 11 of an actuating unit 14 relative to one another, as illustrated with the aid of FIGS. 1 to 4 and 5(a), it is possible for the supporting disks 56, 53 to execute only a rotary movement relative to one another as a result of appropriately arranging the actuating elements 12 and of the fashioning of articulated member 24 and articulated bearing 25. To this end, articulated member 24 and articulated bearing 25 are firstly designed such that they permit only a rotary movement of the upper supporting disk 56 in FIGS. 5(a) to (d) in relation to the longitudinal carrier 52 of the support segment 51. As illustrated in FIG. 5(b), the two actuating elements 12, which are indicated as artificial muscles, are arranged in a V-shaped fashion such that the contraction of the right-hand actuating element 12 in the drawing has executed a rotation of the upper supporting disk 56 in relation to the lower one in the direction of the arrow d.

If the right-hand actuating element 12 is now relieved of load and, at the same time, pressure is applied to the left-hand actuating element 12, the first of these can be lengthened while the second contracts, in order to move the upper supporting disk 56 back against the direction of the arrow d.

The two actuating elements 12 that are shown in FIG. 5(c) in an X-shaped arrangement work in a corresponding way.

Instead of the actuating elements 12 provided between the two supporting disks 56, 53, it is also possible to equip the supporting disks 56, 53 with bearing elements 53', 56' that are illustrated as holding bars and to clamp an actuating element 12' therebetween.

Depending on the intended application, rotary movements and pivoting or tilting movements can be controlled separately by individual actuating units 14. However, it is likewise possible to combine rotary and pivoting/tilting movements in one actuating unit 14.

If use is made in an actuating unit 14 of one or more actuating elements 12 that expand or contract uniformly, it is also possible to attain a lengthening or shortening of the actuating unit 14.

Figure 7:
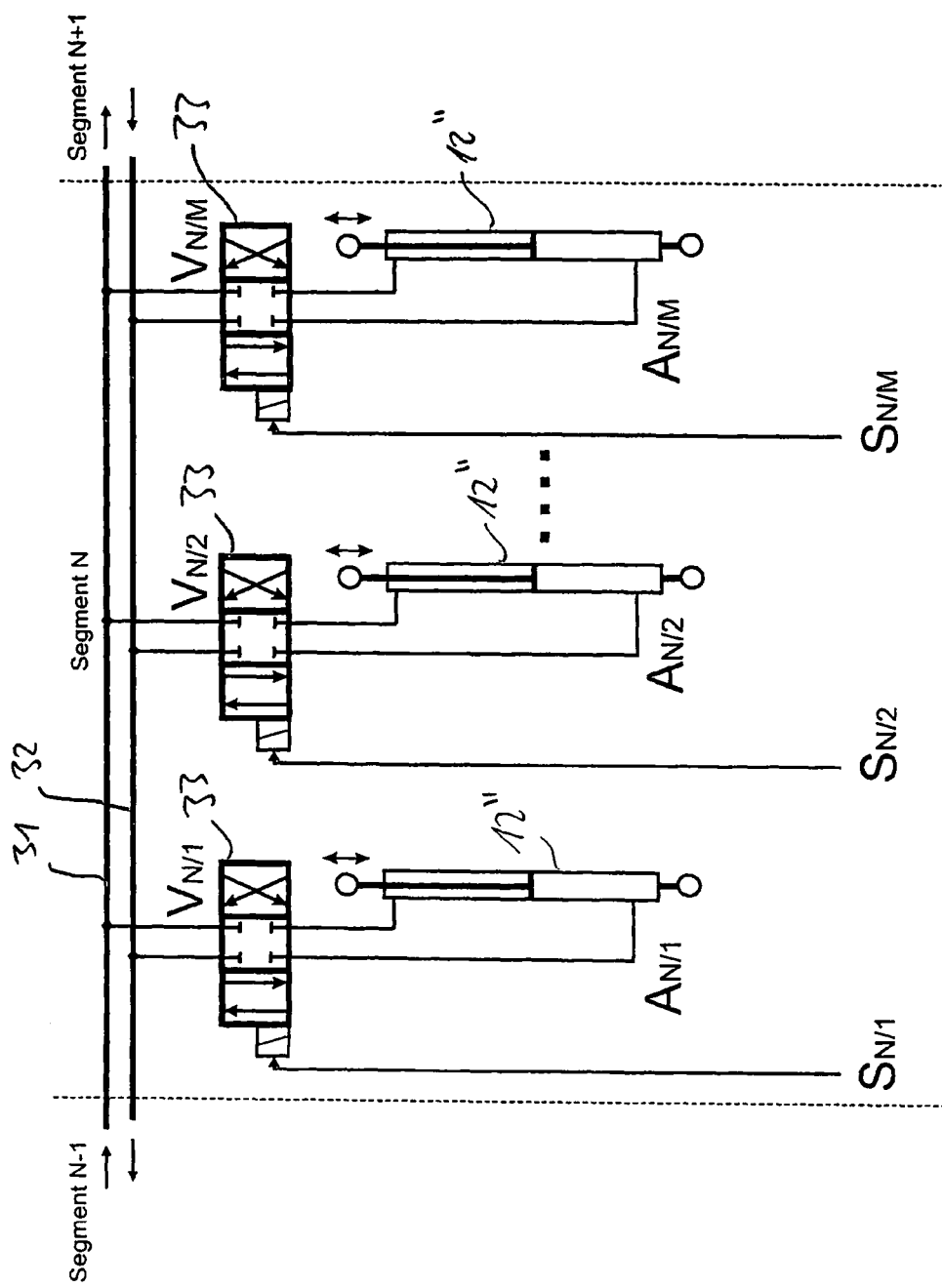
FIG. 7 shows a simplified schematic circuit diagram according to FIG. 6 with the use of pressure cylinders.

Instead of providing the previously described actuating elements 12 that have been described as pneumatic or hydraulic working elements contracting under pressure, in particular as so-called artificial muscles, it is also possible to provide pressure cylinders 12" as actuating elements, as illustrated in FIG. 7. Such pressure cylinders 12", which can be moved in one or the other direction depending on the connection of their working chambers with the feed and discharge lines 31, 32, permit the corresponding supporting elements 11 to be actively adjusted relative to one another in both working directions.

If, as described at the beginning, actuating elements 12 actively working only in one direction are used, it is expedient for the actuating elements 12 to supply a restoring effect upon pressure relief. However, it is also possible for one or more oppositely acting actuating elements 12 to be assigned to each actuating element 12 of an actuating unit 14, as is the case, for example, for the actuating unit 14 described with the aid of FIG. 3.

Instead of furnishing the actuating elements 12 themselves with a restoring effect acting upon pressure relief, it is also possible to assign the individual actuating elements 12 one or more separate restoring elements 61 as indicated in FIG. 1 in the two right-hand actuating units 14.

If, as indicated in FIG. 2 on the right-hand side, there are provided in one or more of the actuating units of the inventive worm-like mechanism tension and/or compression spring elements 63 that support the mechanism internally in order to balance static forces which are to be expected in a planned position of use of said mechanism, these spring elements can, if appropriate, likewise also serve at the same time as restoring elements for the actuating elements 12. Such tension or compression spring elements can in this case also be designed as an enveloping spring arrangement arranged around the worm-like mechanism.

Instead of using the pneumatic or hydraulic actuating elements 12, it is also possible to use piezoelectric actuators as actuating elements 12. Piezoelectric actuators are particularly suitable for worm-like mechanisms that may have only a very small diameter.

The invention claimed is:

1. A worm-like mechanism having:
   a support structure extending in the longitudinal direction of the mechanism, and
   at least two actuating units arranged one behind another in the longitudinal direction of the support structure, in which
   each the actuating unit is assigned two supporting elements which are fitted mutually spaced apart in the longitudinal direction on the support structure in a fashion transverse to the longitudinal direction of the support structure, and
   each the actuating unit has at least one hydraulic or pneumatic actuating element that is arranged between the supporting elements, is connected to a feed line for feeding a hydraulicor pneumatic working medium, and by means of which the supporting elements can be moved relative to one another, wherein
each of the actuating elements is connected to the feed line via a valve that can be activated via a central line, and
each of the actuating elements at least contracts under appropriate pressure application.

2. The mechanism as claimed in claim 1, wherein the valves have a first open position for connecting the actuating element to the feed line, a closed position and a second open position for letting the working medium out of the actuating element, wherein in the second open position the valves connect the actuating elements to a return line or to an outlet line.

3. The mechanism as claimed in claim 2, wherein the valves can be switched by piezoelements.

4. The mechanism as claimed in claim 1, wherein each the actuating unit has a driver circuit that is connected via the central line to a central control circuit and that supplies switching signals for the valves of the actuating unit as a function of control information received from the central control circuit.

5. The mechanism as claimed in claim 4, wherein the driver circuit comprises an open-loop control information processing circuit that generates control signals for valve driver circuits switching the valves, as a function of the received open-loop control information.

6. The mechanism as claimed in claim 4, wherein each of the actuating units has one or more movement sensors whose output signals are detected by the driver circuit.

7. The mechanism as claimed in claim 6, wherein the driver circuit has a transmission circuit for transmitting the output signals from the one or more movement sensors to the central control circuit.

8. The mechanism as claimed in claim 6, wherein the driver circuit has a closed-loop controller circuit to which, as closed-loop control information, the open-loop control information received from the central control circuit and the output signals from the one or more movement sensors are fed, and that supplies open-loop control signals for the valve driver circuits switching the valves as a function of the closed-loop control information.

9. The mechanism as claimed in claim 6, wherein provided as the movement sensors are one or more strain gauges that are fitted on the support structure.

10. The mechanism as claimed in claim 6, wherein provided as the movement sensors are one or more plunger coils that are arranged between the supporting elements of the actuating unit to detect the relative movement thereof.

11. The mechanism as claimed in claim 6, wherein provided as the movement sensor is an optical position detector with a light source and a position-sensitive photoreceiver that are respectively arranged on elements of the actuating unit that can be moved toward one another, the position detector supplying an output signal corresponding to the relative movement between these elements.

12. The mechanism as claimed in claim 1, wherein pressure cylinders are provided as the actuating elements.

13. The mechanism as claimed in claim 1, wherein provided as the actuating elements are pneumatic or hydraulic working elements contracting under pressure.

14. The mechanism as claimed in claim 13, wherein the actuating elements supply a restoring effect upon pressure relief.

15. The mechanism as claimed in claim 13, wherein one or more oppositely actuating elements are assigned to each the actuating element of the actuating unit.

16. The mechanism as claimed in claim 13, wherein one or more restoring elements are assigned to the actuating elements.

17. The mechanism as claimed in claim 1, wherein the at least one actuating element is arranged in the actuating unit such that upon activation the actuating element effects a change in the length of the actuating unit.

18. The mechanism as claimed in claim 1, wherein two, three or more actuating elements are arranged in an actuating unit such that upon appropriate activation the actuating elements effect a defined tilting of the two supporting elements toward one another in a defined radial direction.

19. The mechanism as claimed in claim 1, wherein the at least one actuating elements is arranged in an actuating unit such that upon activation the at least one actuating element effects a rotation of the two supporting elements about the longitudinal direction of the support structure.

20. The mechanism as claimed in claim 1, wherein the supporting elements designed as supporting disks that have a passage for the central line.

21. The mechanism as claimed in claim 1, wherein the support structure has a continuously deformable tubular or hose-like carrier on which the supporting element are fastened at defined axial spacings.

22. The mechanism as claimed in claim 1, wherein the support structure comprises a plurality of similar support segments that are modularly interconnected.

23. The mechanism as claimed in claim 22, wherein the support segment comprises:
a first supporting disk that is permanently connected to one end of a longitudinal carrier, and
a second supporting disk that is held pivotably or rotatably on the other end of the longitudinal carrier via an articulated connection, wherein
on a side of the first supporting disk, averted from the longitudinal carrier, the first supporting disk having fastening means for fastening a second supporting disk of an adjacent support segment.

24. The mechanism as claimed in claim 22, wherein the support segment comprises:
a supporting disk permanently connected to one end of a longitudinal carrier, carrying an articulated bearing on a side of the supporting disk averted from the longitudinal carrier, wherein
on the other end of the longitudinal carrier, the longitudinal carrier carrying on an articulated member corresponding to the articulated bearing such that the longitudinal carrier of the actuating unit can be pivotably or rotatably supported in a articulated bearing on a supporting disk of a next actuating unit.

25. The mechanism as claimed in claim 1, wherein provided in one or more of the actuating units are tension spring or compression spring elements or tension spring and compression spring elements, that support the mechanism internally in order to balance static forces which are to be expected in a planned position of use of said mechanism.

26. The mechanism as claimed in claim 13, wherein artificial muscles are provided as actuating elements.

27. A modular actuating unit for a worm-like mechanism, having
a first supporting plate and a second supporting plate, that extend transverse to the longitudinal direction of a longitudinal carrier, wherein
the first supporting plate is permanently connected to one end of the longitudinal carrier,
the second supporting plate is held pivotably or rotatably or pivotably and rotatably on the other end of the longitudinal carrier via an articulated connection,
on a side of the first supporting place, averted from the longitudinal carrier, the first supporting plate has fastening means for fastening a second supporting plate of an adjacent actuating unit, and at least one hydraulic or pneumatic actuating element that is arranged between the supporting plates, that can be connected to a feed line for feeding a hydraulic or pneumatic working medium, and by means of which the supporting plates can be moved relative to one another, wherein each of the actuating elements can be connected to the feed line via a valve that can be activated via a central line, each of the actuating elements at least contracts upon appropriate pressure application.

* * * * *